United States Patent [19]

Kerkhoffs et al.

[11] Patent Number: 4,880,737

[45] Date of Patent: Nov. 14, 1989

[54] PROCESS FOR THE PREPARATION OF L-ALPHA-AMINO ACID AND D-ALPHA-AMINO ACID AMIDE

[75] Inventors: Pieter L. Kerkhoffs, Geleen; Wilhelmus H. J. Boesten, Sittard, both of Netherlands

[73] Assignee: Stamicarbon B.V., Netherlands

[21] Appl. No.: 792,006

[22] Filed: Oct. 28, 1985

[30] Foreign Application Priority Data

Nov. 15, 1984 [NL] Netherlands ........................ 8403487

[51] Int. Cl.$^4$ ...................... C12P 13/04; C12P 13/08; C12P 13/22; C12N 9/78
[52] U.S. Cl. .................................. 435/106; 435/115; 435/108; 435/227; 435/228; 435/253.3; 435/280
[58] Field of Search ............... 435/106, 228, 280, 877, 435/108, 115, 227, 253.3; 564/163, 193; 562/433, 553

[56] References Cited

U.S. PATENT DOCUMENTS 3,971,700   7/1976   Boesten ............................... 435/280
4,080,259   3/1978   Boesten et al. ...................... 435/228

FOREIGN PATENT DOCUMENTS 1548032   7/1979   United Kingdom ................. 564/126

OTHER PUBLICATIONS

Neilands et al., "Isolation Methods", in *Outlines of Enzyme Chemistry*, pp. 21–33, John Wiley and Sons, Inc., 1955.

Greenstein et al., "Synthesis of γ-Amino Acids" in *Chemistry of the Amino Acids* pp. 697–714, John Wiley and Sons, Inc., 1961.

"Commercial Applications of Immobilized Microorganism Cells." SRI Report No. 139, (1981), pp. 181–182.

Fong, Wing Sien., "Enzyme Technology." SRI International, Process Economics Program Report No. 139 (Jan. 1981), Complete Text, pp. 1–255, (including Table of Contents and 4 Sheets of Drawings).

*Primary Examiner*—Charles F. Warren
*Assistant Examiner*—Gail Knox
*Attorney, Agent, or Firm*—Cushman, Darby & Cushman

[57] ABSTRACT

The invention relates to a process for preparation of L-α-amino acid and D-α-amino acid amide from DL-α-amino-acid amide by contacting the DL-α-amino acid amide in an aqueous solution with an α-amino acid amidase containing preparation obtained from a culture of *Pseudomonas putida* in the presence of traces of bivalent metal ions as activator, characterized in that the aqueous solution also contains a potassium salt selected from the group consisting of potassium sulphate and potassium chloride.

The invention further relates to a process for the preparation of L-α-amino acid and D-α- amino acid amide starting from the corresponding aldehyde, potassium cyanide and ammoniumsulphate, subsequent treatment with a ketone and potassiumhydroxide and finally subjecting to enzymatic hydrolysis with a preparation obtained from *Pseudomonas putida*.

5 Claims, No Drawings

PROCESS FOR THE PREPARATION OF L-ALPHA-AMINO ACID AND D-ALPHA-AMINO ACID AMIDE

The invention relates to a process for the preparation of L-α-amino acid and D-α-amino acid amide from DL-α-amino acid amide by contacting the DL-α-amino acid amide acid amide in an aqueous solution with an α-amino acyl amidase containing preparation obtained from a culture of *Pseudomonas putida* in the presence of traces of bivalent metal ions as activator. Such a process is known from U.S. Pat. No. 4,080,259. In said patent, magnesium, manganese and zinc compounds are mentioned as activator for the α-amino acyl amidase activity (also referred to as amino peptidase activity) of preparations obtained from micro-organisms of the Pseudomonas genus. In itself it had been known for quite some time that, for instance, leucine-amino peptidase (the activity of which in fact corresponds with that of the subject α-amino acyl peptidase) is activated by bivalent manganese ions and magnesium ions, vide Methods in Enzymology, II, p. 93 (1955), Academic Press Inc., New York. Other enzymes, too, may be activated by bivalent metal ions, vide for instance SRI report No. 139, pp. 181–2 (1981).

Such metal ions occur in trace concentrations, i.e. in concentrations of lower than 1 mmole/l. The effect of these ions on the enzyme activity can be very pronounced. In view of this, where possible in enzymic reactions use will be made of such activators. The reference solution for the invention therefore is an α-amino acyl amidase containing aqueous solution of pure DL-α-amino acid amide in which traces of bivalent metal ions are present as activator.

In practice, the dry enzyme preparations already contain such trace elements, for as a rule they are added in the fermentor, where the micro-organism is cultivated. After cultivation, the trace elements automatically end up in an, optionally dried, enzyme preparation.

Applicant has found that in a very practical embodiment of the process as described in the preamble, the activity of the enzyme preparation in the solution often is lower than that of a reference solution containing the same amount of enzyme preparation. In said practical embodiment the process described above is applied in the same aqueous solution as hat in which the DL-α-amino acid amide is synthesized. This renders expensive, interim working up of this DL-α-amino acid amide superfluous.

A customary synthesis for DL-α-amino acid amide proceeds via the so-called Strecker synthesis, in which an aldehyde is coupled to a cyanide and an ammonium salt, yielding a DL-α-amino nitrile. The DL-α-amino nitrile thus obtained can subsequently be treated with a ketone in a strongly basic medium, upon which the DL-α-amino acid amide is formed. This amino nitrile conversion is described in British patent specification 1 548 032. Another possible way of converting DL-α-amino nitrile into the corresponding DL-α-amino acid amide is by treating it with concentrated sulphuric acid, followed by neutralization with a hydroxide.

Applicant now has found that the activity of the α-amino acyl amidase preparation obtained from a culture of *Pseudomonas putida* is at least in part inhibited (relative to the reference solution) by sodium ions. These sodium ions may, for instance, originate from sodium cyanide, used in the Strecker synthesis, and/or from sodium hydroxide, used in the conversion of DL-α-amino nitrile. Yet other causes of the sodium ions' presence in the solution are conceivable, but actually it is irrelevant how these ions have entered the solution. So far, sodium ions had not been known to have such an inhibitory effect on α-amino acyl amidase preparations of *Pseudomonas putida*.

Applicant moreover has found that it is not only sodium that has an effect on the enzyme activity in the practical embodiment of the enzymic separation, but that the counter ion, for instance the anion of the ammoniumsalt in the Strecker synthesis (it should be noted that many different ammonium salts can in principle be applied in the strecker synthesis) also affects this activity. Thus applicant has found that, for instance, nitrate, acetate and biphosphate ions have an inhibitory effect relative to the reference solution.

Anions, too, had so far not been known to affect the activity of α-amino acyl amidase from *Pseudomonas putida*.

The object of the invention is to provide a solution for the disadvantageous effects of inhibition, with which applicant was confronted when carrying out the process as described in the preamble.

A further object of the invention is to provide a process as described in the preamble in which the enzyme activity is even increased relative to the reference solution.

The process according to the invention for the preparation of L-α-amino acid and D-α-amino acid amide from DL-α-amino acid amide by contacting the DL-α-amino acid amide in an aqueous solution with an α-amino acyl amidase containing preparation obtained from a *Pseudomonas putida* culture in the presence of traces of bivalent metal ions as activator is characterized in that the aqueous solution also contains a potassium salt chosen from the group consisting of potassium sulphate and potassium chloride. This allows the reduction of the amount of α-amino acyl amidase used in the enzymic separation, which yields a clear cost price advantage. This advantage amply offsets the high price, compared with sodium compounds, of the potassium compounds.

Where sodium, in whichever salt form, has an inhibitory effect on the enzyme, it is surprising that potassium in the properly chosen salt form, i.e. as chloride or, by preference, as sulphate, should have an activating effect on the enzyme.

The process according to the invention of course is not restricted to the practical embodiment as described above, but in general comprises the enzymic separation of DL-α-amino acid amides in an aqueous solution. The way this aqueous solution is prepared is less important.

In the process according to the invention, per litre of aqueous solution 0.1-3 moles potassium can be applied as sulphate or as chloride.

The process according to the invention in principle relates to α-amino acyl amidase containing preparations from the *Pseudomonas putida* strain as well as from mutants thereof. A highly suitable *Pseudomonas putida* strain is registered under number 12633 in the American Type Culture Collection at Washington D.C., U.S. of America.

A preparation having α-amino acyl amidase activity can be obtained by precipitation of the cells of *Pseudomonas putida*, optionally use being made of a flocculating agent. The cells can also be crosslinked or they can be bonded to or absorbed on a carrier. In some cases it may be desirable to modify the cell walls, for instance by a heat treatment or by chemical treatment (for instance with toluene), to make the enzyme better accessible. A crude preparation can also be obtained by destroying the cell walls and recovering the enzyme by extraction, filtration and optionally by spray drying.

A preparation consisting of the pure enzyme can be obtained in conventional manner from the crude product referred to above. Crude or pure enzyme preparations can also be immobilized on a carrier, as can entire cells.

The preparation having α-amino acyl amidase activity is contacted with the DL-α-amino acid amide in an aqueous medium at a temperature of between 0° and 60° C., and by preference at a temperature of between 0° and 40° C., and at a pH of between 6 and 10.5, and by preference of between 7.5 and 9.5.

Outside these ranges, the activity and/or stability of the enzyme generally is inadequate for practical use.

The weight ratio of the (unpurified) enzyme preparation to the substrate may vary widely, for instance between 1 : 25 and 1 : 750. If a pure enzyme is used, a higher ratio can be applied.

Upon completion of hydrolysis of the L-α-amino acid amide, the free acid can be separated from the remaining D-α-amino acid amide and the latter compound can subsequently also be hydrolyzed, yielding D-α-amino acid.

If the D-α-amino acid amide can be dissolved together with the L-α-amino acid (as is the case with D-phenyl glycine amide and D-valine amide), the D-α-amino acid can be obtained in the following way. To the above-mentioned mixture an aldehyde, for instance benzaldehyde, is added in an amount that is equimolar or higher relative to the D-α-amino acid amide, resulting in formation of an insoluble Schiff base of the D-α-amino acid amide (D-N-benzylidene compound of D-α-amino acid amide). The Schiff base can, after separation, subsequently be hydrolyzed to the D-α-amino acid using a strong acid.

The process according to the invention is suitable for isolating optically active natural or synthetic-amino acids and/or D-α-amino acid amides, such as the D and/or L form of phenylalanine, 3,4-dihydroxyphenylalanine, homophenylalanine, tyrosine, methionine, valine, leucine, alanine, phenylglycine, 4-hydroxyphenylglycine, 4-alkoxyphenylglyine and other substituted phenylglycines. The essence of the process according to the invention is that the enzyme can be activated, independently of the substrate.

A preferred practical embodiment of the preparation of an L-α-amino acid and a D-α-amino acid amide, starting from an aldehyde, cyanide and ammonium salt, which also comprises the process according to the invention, is as follows: An aldehyde RCHO, where R represents an alkyl or aryl group, substituted or not, is introduced into an aqueous ammonia solution, in which potassium cyanide and ammonium sulphate have also been dissolved. The solution is heated at 40° C. during 1-4 hours. This results in formation of DL-α-amino nitrile

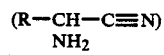

(plus potassium sulphate).

Subsequently, a ketone is added, as well as potassium hydroxide, and DL-α-amino acid amide

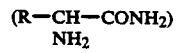

is formed. Now, a high-activity enzymic separation can be effected by addition of an α-amino acyl amidase preparation from *Pseudomonas putida*. If desired, the D-α-amino acid amide can be worked up further to the corresponding D-α-amino acid via Schiff base formation.

The invention will be further elucidated on the basis of the following examples.

COMPARATIVE EXAMPLE

In a 50 ml reaction vessel, provided with a heating jacket, 4.4 g DL-valineamide (37.9 mmoles) was dissolved in 39.6 g water which was meanwhile being stirred, and the solution thus obtained was heated to 40° C. Subsequently, 300 mg of a crude, α-amino acyl amidase containing preparation (which contained traces of $Mn^{2+}$ and $Mg^{2+}$) obtained from *Pseudomonas putida* ATCC 12633 was added and the vessel was closed. After 45 minutes a sample was taken and the amount of $NH_3$ (formed in hydrolysis of the L-α-amino acid amide to the corresponding -amino acid) was determined using an ammonia electrode. In this reference solution, 25293 μ moles $NH_3$ were found to have been formed. Converted, the activity of the enzyme was 83 units / gramme, one unit standing for 1 μ mole $NH_3$ formed per minute per gramme of enzyme preparation at a reaction time of 45 minutes and a temperature of 40° C.

EXAMPLE I

In the vessel described in the comparative example, 4.4 g DL-valineamide (37.9 mmoles) and 4.4 g potassium sulphate (25.3 mmoles) were successively dissolved in 35.2 g water, upon which heating to 40° C. took place. Subsequently, 275 mg of the enzyme preparation of the comparative example was added. After 45 minutes the amount of $NH_3$ was determined in the way described above. An activity of 128 units/g was found. From this, the activating effect on the enzyme preparation of the potassium sulphate is apparent.

The influence of various ions is shown in the following table.

TABLE

| DL-α-aminoacidamide in water | mole/1000 g | Cation in mole/1000 g | | Anion in mole/1000 g | | Activity in U/g enzym | Relative Activity in % |
|---|---|---|---|---|---|---|---|
| DL-valine-amide | 0.86 | — | — | — | — | 83 | 100 |
| (10% wt) | 0.86 | Na$^+$ | 1.7 | Cl$^-$ | 1.7 | 26 | 31.3 |
| | 0.86 | Na$^+$ | 1.4 | SO$_4^{2-}$ | 0.7 | 67 | 80.7 |
| | 0.86 | K$^+$ | 1.34 | Cl$^-$ | 1.34 | 87 | 104.8 |
| | 0.86 | K$^+$ | 1.16 | SO$_4^{2-}$ | 0.58 | 128 | 154.8 |
| | 0.86 | K$^+$ | 1.0 | NO$_3^-$ | 1.0 | 67 | 80.7 |

TABLE-continued

| DL-α-aminoacidamide in water | mole/1000 g | Cation in mole/1000 g | | Anion in mole/1000 g | | Activity in U/g enzym | Relative Activity in % |
|---|---|---|---|---|---|---|---|
| | 0.86 | K+ | 1.14 | HPO$_4^{2-}$ | 0.57 | 34 | 41.0 |
| DL-valine-amide | 1.72 | — | — | — | — | 48 | 100 |
| (20% wt) | 1.72 | K+ | 2.68 | Cl$^-$ | 2.68 | 45 | 93.8 |
| DL-valine-amide | 1.72 | — | — | — | — | 151 | 100 |
| (20% wt) | 1.72 | K+ | 2.27 | CH$_3$COO$^-$ | 2.27 | 50 | 33.1 |
| DL-phenyl-glycine-amide | 0.33 | — | — | — | — | 405 | 100 |
| | 0.33 | Na+ | 0.70 | SO$_4^{2-}$ | 0.35 | 170 | 42.0 |
| (5% wt) | 0.33 | K+ | 0.58 | SO$_4^{2-}$ | 0.29 | 435 | 107.4 |

EXAMPLE II

At room temperature in a 1 litre reaction flask, provided with stirrer, thermometer, cooler, drop funnel and heating jacket, 66 g ammonium sulphate (0.5 mole) was dissolved in 150 ml water and 250 ml ammonia (25% wt) was added while stirring was applied. Subsequently, 65 g potassium cyanide (1.0 mole) and 110 ml water were added. 95 ml isobutaraldehyde (1.0 mole) was through the drop funnel subsequently slowly and dropwise added, the temperature not exceeding 40° C.

To have a complete Strecker reaction, the reaction mixture was stirred for 2.5 hours at the temperature obtained. HPLC analysis showed the DL-α-valinenitrile yield, calculated relative to isobutyraldehyde, to be 93%.

Subsequently, a mixture of 75 ml acetone and 100 ml water was added to this reaction mixture and the pH wa set at 13.3 using 10 ml 8 molar potassium hydroxide solution. The temperature increased from 33° C. to 41° C. in 0.5 hour.

This temperature was maintained for 6 hours, after which 3.0 ml concentrated sulphuric acid was added for neutralization of the potassium hydroxide solution. The flask was subsequently prepared for distillation. In one hour's time 110 ml of a water-ammonia-acetone mixture was distilled overhead, while the bottom temperature rose to 102° C.

Using HPLC analysis the DL-α-valineamide yield was determined. The value found was 88.4%, calculated on the basis of butyraldehyde. The pH of the solution was 9.5. After removal of the potassium sulphate by filtration, the solution was given a temperature of 40° C. and subsequently 15 g of an α-amino acyl amidase containing preparation, obtained from a culture of *Pseudomonas putida* ATCC 12633, was added. After this, stirring was applied for 20 hours at 40 ° C.

Subsequently, 45 ml benzaldehyde was slowly and dropwise added to the solution and stirring was continued at 40° C. for 0.5 hour.

The precipitated D-N-benzylidenevalineamide was filtered off, washed with 4×25 ml water on the filter and dried for 16 hours at 45° C. and 16 mbar. (From the filtrate L-valine can be recovered, if desired). The yield of dry and pure (determined by thin-layer chromatography) D-N-benzylidenevalineamide was 82.6 g. Relative to isobutyraldehyde the efficiency was 40.5%, and relative to valineamide 91.6%.

From the specific rotation $[\alpha]_D^{20} = -12.7$ (CH$_3$OH; C=2.0), a selectivity of 99.6 could be calculated.

To a 1 liter reaction flask suitable for distillation 82.0 g D-N-benzylidenevalineamide and a mixture consisting of 350 ml water and 25 ml concentrated sulphuric acid were added.

In two hours' time 170 ml water and 40 ml benzaldehyde were distilled off. After addition of 75 ml concentrated sulphuric acid, heating was applied for 3 hours at 100° C. After subsequent cooling to 60° C., ammonia (25% wt.) was slowly and dropwise added until the pH was 2.0. To the resulting solution 2.5 g activated carbon was added, following which stirring was applied for 0.5 hour at 60° C. The activated carbon was subsequently filtered off and washed on the filter with 2×5 ml water. The filtrate was neutralized further to pH 5.0 using 25% (wt) ammonia solution. This was attended by crystallization out of D-valine. After cooling to 20° C., the D-valine was filtered off and washed on the filter with 3×25 ml water and 3×25 ml acetone and then dried for 16 hours at 45° C. and 16 mbar. The yield of pure (determined by thinlayer chromatography) and sulphate-free D-valine was 35.4 g. The overall efficiency was 30.3, calculated relative to isobutyraldehyde (it should, however, be noted that in theory only 0.5 mole D-valine can be prepared from 1 mole isobutyraldehyde).

From the specific rotation $[\alpha]_D^{20} = +28.0$ (6 N HCl; C=8), a selectivity of 99.5% could be calculated. The selectivity was calculated as follows:

$$\% D = \frac{50 \cdot [\alpha]_D^{20}}{\max \cdot [\alpha]_D^{20}} \% + 50\%.$$

We claim:
1. Process for the preparation of L-α-amino acid and D-α-amino acid amide from DL-α-amino-acid amide by contacting the DL-α-amino acid amide in an aqueous solution with an α-amino acyl amidase containing preparation obtained from a culture of *Pseudomonas putida* ATCC 12633 in the presence of traces of bivalent metal ions as activator, wherein the aqueous solution also contains a potassium salt selected from the group consisting of potassium sulphate and potassium chloride.

2. Process according to claim 1, wherein the aqueous solution contains 0.1–3 moles potassium ions per liter.

3. Process according to claim 1, wherein the potassium ions are present in the form of potassium sulphate.

4. Process according to claim 1, wherein DL-phenylglycineamide or DL-valineamide is applied as the DL-α-amino acid amide.

5. Process for the preparation of L-α-amino acid having the formula

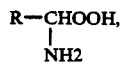

where R represents an unsubstituted or substituted alkyl or aryl group, and a D-α-amino acid amide having the formula

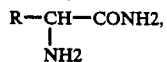

where R signifies the same as above wherein:

(a) an aldehyde having the formula RCHO, where R signifies the same as above, is converted into a DL-α-amino nitrile in an aqueous ammonia solution with potassium cyanide and ammonium sulfate, (b) a ketone and potassium hydroxide are subsequently added to the above solution containing the DL-α-amino nitrile to form DL-α-acid amide and, (c) an α-amino acyl amidase containing preparation, obtained from a culture of *Pseudomonas putida* ATCC 12633, is added along with traces of bivalent metal ions to the solution containing the DL-α-amino acid amide.

* * * * *

UNITED STATES PATENT AND TRADEMARK OFFICE
CERTIFICATE OF CORRECTION

PATENT NO. : 4,880,737
DATED : November 14, 1989
INVENTOR(S) : KERKHOFFS et al.

It is certified that error appears in the above-identified patent and that said Letters Patent is hereby corrected as shown below:

Title page:

In the Abstract, lines 4-5, please correct "α-amino acid amidase" to read --α-amino acyl amidase--;

column 2, line 15, please correct "strecker" to read --Strecker--; and column 5, line 34, please correct "wa" to read --was--.

Signed and Sealed this

Fourteenth Day of May, 1991

Attest:

HARRY F. MANBECK, JR.

Attesting Officer     Commissioner of Patents and Trademarks